United States Patent
Baum et al.

(10) Patent No.: US 12,045,386 B2
(45) Date of Patent: Jul. 23, 2024

(54) METHODS AND SYSTEM FOR REMOTELY CAPTURING MEDIA VIA A USER INTERFACE BIDIRECTIONALLY LINKED TO A REMOTE SERVER

(71) Applicant: Harrow IP, LLC, Nashville, TN (US)

(72) Inventors: Mark L. Baum, Nashville, TN (US); Andrew E. Livingston, Nashville, TN (US); Ryan Kibler, Nashville, TN (US)

(73) Assignee: HARROW IP, LLC, Nashville, TN (US)

( * ) Notice: Subject to any disclaimer, the term of this patent is extended or adjusted under 35 U.S.C. 154(b) by 111 days.

(21) Appl. No.: 17/747,616

(22) Filed: May 18, 2022

(65) Prior Publication Data
US 2022/0374075 A1    Nov. 24, 2022

Related U.S. Application Data
(60) Provisional application No. 63/190,215, filed on May 18, 2021.

(51) Int. Cl.
| | | |
|---|---|---|
| *G06F 3/01* | (2006.01) | |
| *H04N 23/69* | (2023.01) | |
| *H04N 23/73* | (2023.01) | |

(52) U.S. Cl.
CPC ............. *G06F 3/013* (2013.01); *H04N 23/69* (2023.01); *H04N 23/73* (2023.01)

(58) Field of Classification Search
None
See application file for complete search history.

(56) References Cited

U.S. PATENT DOCUMENTS

| | | | | |
|---|---|---|---|---|
| 9,672,370 | B1* | 6/2017 | Lewis | H04N 21/4532 |
| 10,108,871 | B2* | 10/2018 | Derakhshani | G01S 15/89 |
| 10,111,103 | B2* | 10/2018 | Derakhshani | G06V 10/141 |
| 2012/0113209 | A1* | 5/2012 | Ritchey | G06F 3/015 |
| | | | | 348/14.02 |
| 2016/0255305 | A1* | 9/2016 | Ritchey | H04N 7/15 |
| | | | | 348/14.03 |
| 2017/0061210 | A1* | 3/2017 | Ollila | H04N 1/00307 |
| 2018/0041503 | A1* | 2/2018 | Lindemann | H04L 63/061 |
| 2019/0164156 | A1* | 5/2019 | Lindemann | H04L 9/3247 |
| 2019/0177993 | A1* | 6/2019 | Shell | E04H 1/12 |
| 2020/0218878 | A1* | 7/2020 | Mequanint | G08B 21/182 |
| 2020/0311235 | A1* | 10/2020 | Storm | G06F 3/0346 |
| 2021/0117527 | A1* | 4/2021 | Behm | G07C 9/37 |
| 2021/0350550 | A1* | 11/2021 | Stengel | G06V 40/19 |
| 2022/0004617 | A1* | 1/2022 | Irwin, III | G06F 21/40 |
| 2022/0279096 | A1* | 9/2022 | Katz | H04N 23/55 |

* cited by examiner

*Primary Examiner* — Talha M Nawaz
(74) *Attorney, Agent, or Firm* — Norton Rose Fulbright US LLP

(57) ABSTRACT

Some embodiments of the present disclosure present methods and systems for remotely capturing an image of an eye of a user via a user interface bidirectionally linked to a remote server that is configured to anonymize data communicated from the user device. In some embodiments, a user device may activate its camera after receiving a request at the user interface from the remote server. Further, the user interface may determine a zoom level for the camera to capture the image of the eye of the user facing the camera and capture the image based on the determined zoom level. In some instances, the user device may transmit the data including the captured image to the remote server via an encrypted bi-directional communication link.

15 Claims, 5 Drawing Sheets

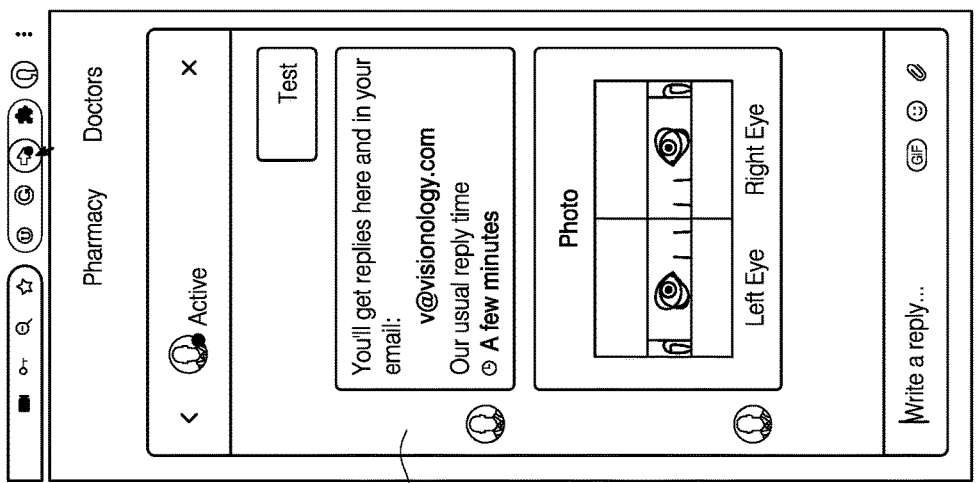
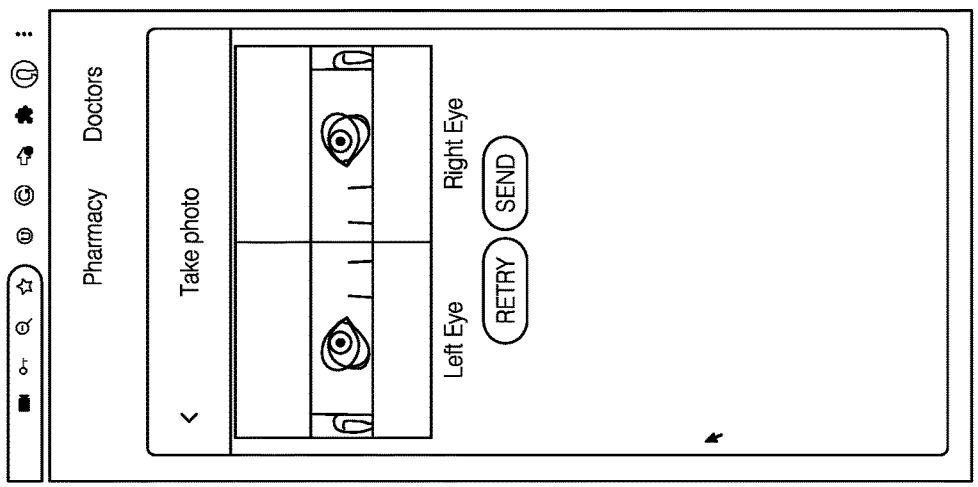
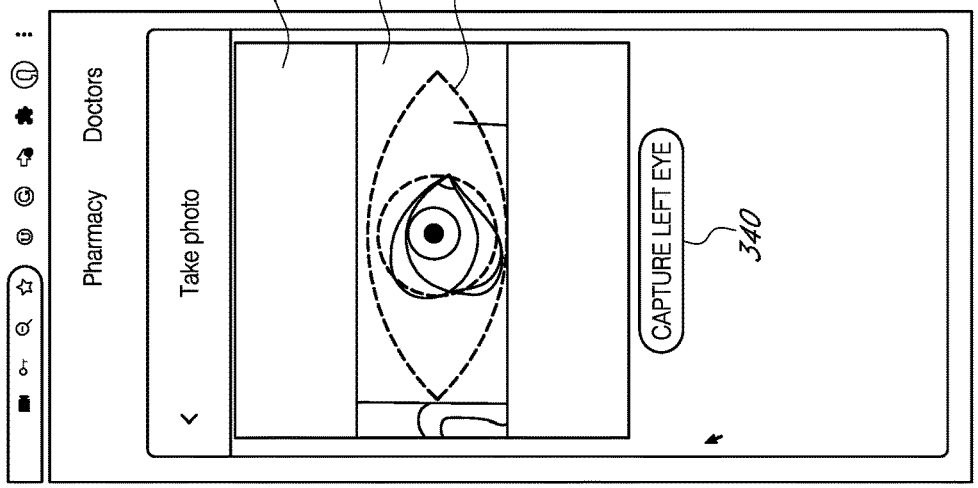
FIG. 3C
FIG. 3B
FIG. 3A

METHODS AND SYSTEM FOR REMOTELY CAPTURING MEDIA VIA A USER INTERFACE BIDIRECTIONALLY LINKED TO A REMOTE SERVER

CROSS-REFERENCE TO RELATED APPLICATIONS

The present application claims the benefit of U.S. Provisional Application No. 63/190,215, filed on May 18, 2021, the contents of which are incorporated herein by reference as if set forth in full.

FIELD OF THE INVENTION

The present specification generally relates to remotely capturing media via a bidirectionally linked user interface, and more specifically, to remotely capturing an image and/or video of an eye of a user via a user interface bidirectionally linked to a remote server.

BACKGROUND

Some patients with eye diseases and conditions may not have convenient access to ophthalmological diagnoses and treatment facilities. Some of the diseases and conditions, however, can be diagnosed, and appropriate treatments can be prescribed, remotely if eye health care providers such as ophthalmologists are able to obtain access to images/videos of the eyes of patients for which diagnoses/treatments are sought. As such, there is a need for methods and a system that allow for remote capturing of images/videos of eyes of patients.

SUMMARY

The following summarizes some aspects of the present disclosure to provide a basic understanding of the discussed technology. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in summary form as a prelude to the more detailed description that is presented later.

In some embodiments of the present disclosure, a method comprises receiving, from a remote server and at a user interface of a user device having a camera, a request to capture an image of an eye of a user facing the camera, the user interface in communication with the remote server via an encrypted bi-directional communication link and the remote server configured to anonymize data communicated from the user device. Further, the method comprises receiving, in response to the receiving the request and at the user interface of the user device, an authorization to activate the camera of the user device. In addition, the method comprises activating, in response to the receiving the authorization and via a processor of the user device, the camera of the user device. The method also comprises determining, via the processor, a zoom level for the camera to capture the image of the eye of the user facing the camera. Further, the method comprises capturing, via the camera, the image of the eye of the user using the determined zoom level for the camera. In addition, the method comprises transmitting, via a transceiver of the user device, the data including the captured image of the eye to the remote server via the encrypted bi-directional communication link.

Some embodiments of the present disclosure comprise a non-transitory memory storing instructions and one or more hardware processors coupled to the non-transitory memory and configured to read the instructions from the non-transitory memory to cause the system to perform operations. The operations comprise receiving, from a remote server and at a user interface of a user device having a camera, a request to capture an image of an eye of a user facing the camera, the user interface in communication with the remote server via an encrypted bi-directional communication link and the remote server configured to anonymize data communicated from the user device. Further, the operations comprise receiving, in response to the receiving the request and at the user interface of the user device, an authorization to activate the camera of the user device. In addition, the operations comprise activating, in response to the receiving the authorization and via a processor of the user device, the camera of the user device. The operations also comprise determining, via the processor, a zoom level for the camera to capture the image of the eye of the user facing the camera. Further, the operations comprise capturing, via the camera, the image of the eye of the user using the determined zoom level for the camera. In addition, the operations comprise transmitting, via a transceiver of the user device, the data including the captured image of the eye to the remote server via the encrypted bi-directional communication link.

Some embodiments of the present disclosure comprise a non-transitory computer-readable medium having stored thereon computer-readable instructions executable to cause performance of operations. The operations comprise receiving, from a remote server and at a user interface of a user device having a camera, a request to capture an image of an eye of a user facing the camera, the user interface in communication with the remote server via an encrypted bi-directional communication link and the remote server configured to anonymize data communicated from the user device. Further, the operations comprise receiving, in response to the receiving the request and at the user interface of the user device, an authorization to activate the camera of the user device. In addition, the operations comprise activating, in response to the receiving the authorization and via a processor of the user device, the camera of the user device. The operations also comprise determining, via the processor, a zoom level for the camera to capture the image of the eye of the user facing the camera. Further, the operations comprise capturing, via the camera, the image of the eye of the user using the determined zoom level for the camera. In addition, the operations comprise transmitting, via a transceiver of the user device, the data including the captured image of the eye to the remote server via the encrypted bi-directional communication link.

BRIEF DESCRIPTION OF THE DRAWINGS

FIGS. 3A-3C show example illustrations of the remote capturing of an image of user's eyes via a chat window operating on a user interface that is bidirectionally linked to a remote server, according to various aspects of the present disclosure.

Figure 1:
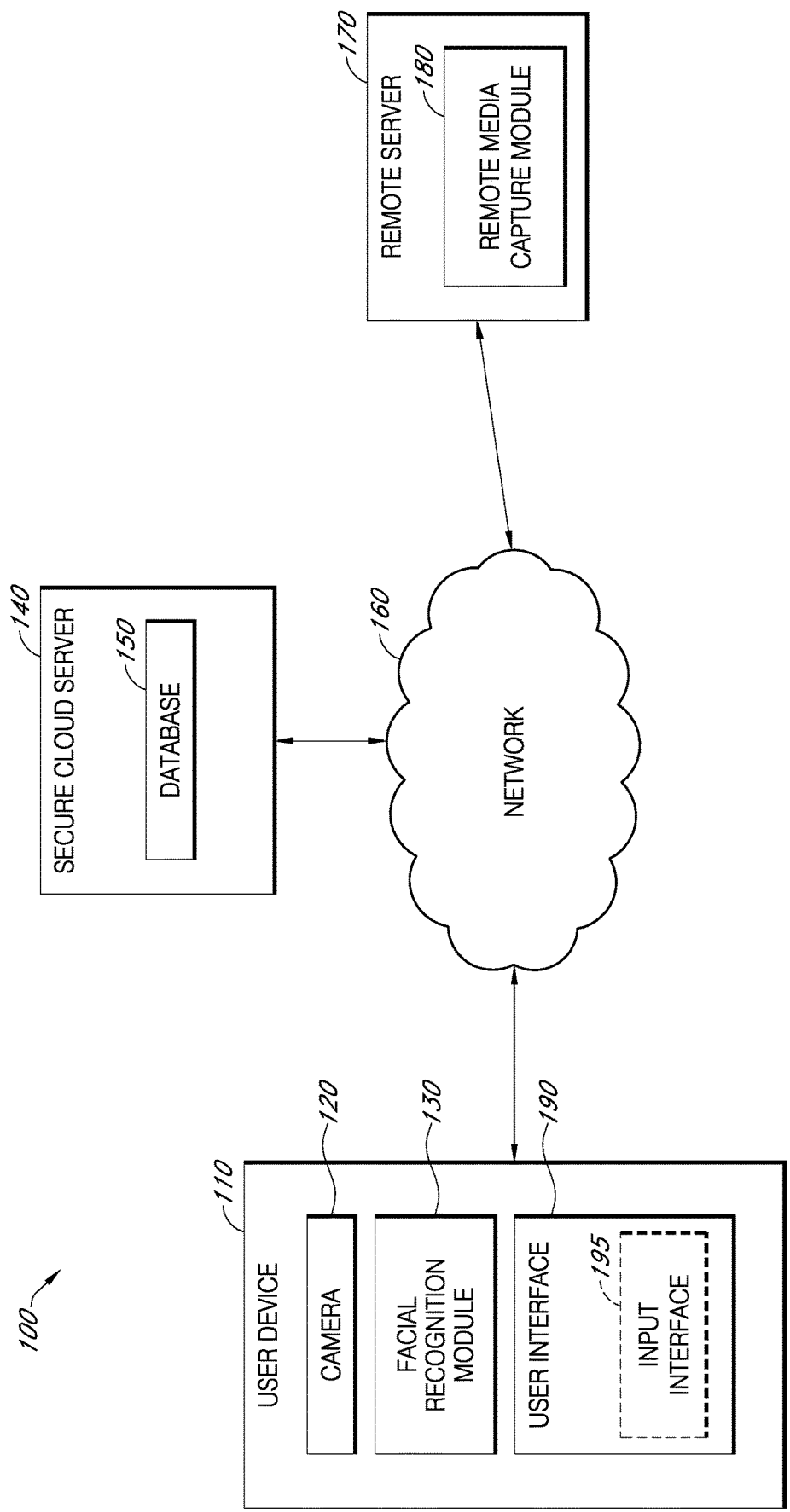
FIG. 1 is a block diagram of a networked system, according to various embodiments of the present disclosure.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The following description of various embodiments is exemplary and explanatory only and is not to be construed as limiting or restrictive in any way. Other embodiments, features, objects, and advantages of the present teachings will be apparent from the description and accompanying drawings, and from the claims. Unless defined otherwise, all technical and scientific terms used herein have the same meaning as commonly understood by one of ordinary skill in the art to which this invention belongs.

The present disclosure pertains to methods and systems for remotely capturing a media via a user interface that is bidirectionally linked to a remote server. In some instances, the user may be a patient with an eye disease or condition and may be seeking diagnoses and/or treatment remotely from a health care provider, such as but not limited to, an ophthalmologist. For example, with reference to FIG. 1, the patient may have on her/his user device 110 a user interface 190 that allows the patient to remotely access the remote server 170, for example, of the health care provider. The user device 110 can be a smartphone, a tablet computer, a personal computer, etc., and the user interface 190 can be a web browser or an application user interface of an application operating on the user device 110.

FIG. 1 is a block diagram of a networked system 100 suitable for remotely capturing media via a bidirectionally linked user interface, according to an embodiment. Networked system 100 may comprise or implement a plurality of servers and/or software components that operate to perform various payment transactions or processes. Example servers may include, for example, stand-alone and enterprise-class servers operating a server OS such as a MICROSOFT™ OS, a UNIX™ OS, a LINUX™ OS, or other suitable server-based OS. It can be appreciated that the servers illustrated in FIG. 1 may be deployed in other ways and that the operations performed and/or the services provided by such servers may be combined or separated for a given implementation and may be performed by a greater number or fewer number of servers. One or more servers may be operated and/or maintained by the same or different entities.

In some embodiments, the system 100 may include the user device 110, a secure storage/cloud server 140, and a remote server 170 that are in communication with one another over a network 160. In some embodiments, the user device 110, a secure storage/cloud server 140, and a remote server 170 may each include one or more electronic processors, electronic memories, and other appropriate electronic components for executing instructions such as program code and/or data stored on one or more computer readable mediums to implement the various applications, data, and steps described herein. For example, such instructions may be stored in one or more computer readable media such as memories or data storage devices internal and/or external to various components of system 100, and/or accessible over network 160. Although only one of each the user device 110, a secure storage/cloud server 140, and a remote server 170 are shown, there can be more than one of each user device, secure storage/cloud server, or remote server, in accordance with various embodiments.

In some embodiments, the network 160 may be implemented as a single network or a combination of multiple networks. For example, in various embodiments, network 160 may include the Internet or one or more intranets, landline networks, wireless networks, virtual networks, public networks, private networks, and/or other appropriate types of networks. In another example, the network 100 may comprise a wireless telecommunications network (e.g., cellular phone network) adapted to communicate with other communication networks, such as the Internet.

In some embodiments, user device 110 may be implemented using any appropriate hardware and software configured for wired and/or wireless communication over network 160. For example, in some embodiments, the user device 110 may be implemented as a handheld and/or portable user device and in yet some embodiments, the user device 110 may be implemented as a non-portable and/or non-handheld user device. For example, the user device 110 can be a non-portable and/or non-handheld desktop or personal computer (PC). And in other examples, the user device 110 can be a portable and/or a handheld smart phone, a smart phone with additional hardware such as NFC chips, BLE hardware etc., wearable devices with similar hardware configurations such as a gaming device, a Virtual Reality Headset, or that talk to a smart phone with unique hardware configurations and running appropriate software, laptop computer, and/or other types of computing devices capable of transmitting and/or receiving data, such as an iPad™ from Apple™.

Upon activation of the user interface 190 by the user, in some embodiments, the user interface 190/user device 110 may be connected to the remote server 170 of the health care provider over the network 160 via a secure (e.g., encrypted) bidirectional communication link. In some instances, the communication link may utilize secure socket layer (SSL) protocols configured to secure data communicated therewith. That is, the communication link may be configured such that data communicated via the communication link, such as but not limited to patient health information, may be encrypted during the transport of the data via the communication link. In some cases, the communication link may be configured to comply with the security requirements of the Health Insurance Portability and Accountability Act (HIPAA) that are related to the handling of patient data, i.e., the communication link may be HIPAA-compliant.

In some embodiments, the user interface 190 may include an input interface 195 that allows the user to communicate with the remote server 170 of the health care provider. For example, the input interface 195 can be a chat window (e.g., chat window 220 of FIG. 2) that allows the user to input requests, replies, preferences, etc. to be transmitted to the remote server 170. In some cases, the user may input into the input interface 195 an indication that the user is seeking medical diagnosis or treatment for an eye disease or condition. For example, when the user activates the user interface 190, a chat window 195, such as chat window 220 of FIG. 2, may automatically pop up in the user interface 190 of the user device 110, and allow the user to request a service from the health care provider (e.g., via the remote server 170), for instance by providing multiple options the user to choose from in the chat window. In some cases, the chat window may automatically pop up and prompt the user to provide patient health information (PHI) data which may then be provided to the health care provider after being transmitted to the remote server 170 via the bidirectional communication link. It is to be understood that the above are non-limiting examples and that all aspects related to a user interacting via a chat window of a user interface 190 that is in communication with a remote server 170 to provide the remote server 170 medical and related information are contemplated.

In some embodiments, a remote media capture module 180 executing at the remote server 170 may be configured to communicate with the user via the user interface 190, e.g., via the input interface 195. For example, after the activation of the user interface 190 including the input interface, the remote media capture module 180 may transmit an instruction to the user device 110. In some cases, the instruction may request the user interface 190 to display at the chat window a prompt requesting the user to provide PHI data. In some instances, instead of or in addition to the remote media capture module 180, a live person may also be able to communicate, using the remote server 170, with the user via the user interface 190 of the user device 110 to prompt the user to provide the PHI data.

In some embodiments, the prompt for the PHI data may request the user to provide, via the chat window of the user interface 190, an image and/or video of an eye of the user. For example, the prompt in the chat window may request for the user to authorize the activation of the camera 120 so that an image/video of the eye of the user may be captured. In some embodiments, the captured image/video of the eye of the user may be transmitted to the remote server 170 and/or another storage server (e.g., cloud server) 140 from the chat window as PHI data. In some instances, the user may authorize the activation of the camera 120 (e.g., by tapping, clicking, etc., on the prompt) and the camera 120 may be activated, with the scene to be captured as an image/video shown within the user interface 190. In some cases, the scene in the chat window of the input interface 195 may include outlines or indications superimposed thereon to guide the user in facing the camera 120 so that the user's eye the image and/or video of which is being captured is within the scene.

In some embodiments, the focus of the camera 120 may be determined based on the type of the user device 110. For example, the instruction or request from the remote media capture module 180 to prompt the user to provide PHI data may also include settings specifying the focus or zoom level the camera 120 may use to capture the image of the eye of the user, where the settings may be based on the type of the user device 110. For instance, the settings may specify a first pre-set zoom level if the user device 110 is a handheld and/or portable user device (e.g., smartphone, tablet computer, laptop, etc.), and a second pre-set zoom level if the user device 110 is a non-portable and/or non-handheld user device (e.g., desktop computers, etc.). This is because, the distance from a user device 110 to a user when the user is utilizing the user device 110 may in general depend on the type of the user device 110. For example, users tend to hold portable devices closer to their faces/eyes as compared to the separation distance between their faces and monitors of desktops on which cameras are usually located. As such, in some cases, the first pre-set zoom level may be lower than the second pre-set zoom level. That is, the camera 120 may zoom more when the user device 110 is a non-portable and/or non-handheld user device compared to when the user device 110 is a handheld and/or portable user device.

Accordingly, after the activation of the camera 120 as authorized by the user, the camera 120 may adjust its focus based on the zoom level settings so that the camera focuses on the eyes/face of the user. In some instances, the zoom level settings may not result in the camera 120 focusing on the eyes/face of the user. In such cases, the user device 110 may post a notice on the user interface 190 or chat window requesting that the user change her/his position with respect to the camera 120 so that the camera 120 can focus on the eyes/face. That is, the notice may request that the user shift their position such that the camera 120 can focus on the user's eyes/face when focusing at the selected zoom level.

In some embodiments, the user device 110 may use a facial recognition module 130 of the user device 110 to measure or estimate the distance from the face/eyes of the user to the camera 120 on the user device 110 and adjust the zoom level of the camera 120 accordingly. For instance, an iPhone® user device may activate its Face ID® module to measure a distance from the camera 120 of the user device 110 to the face/eyes of the user of the iPhone® and adjust the zoom level of the camera 120 based on the distance such that the camera 120 focuses on the eyes/face. In some instances, the measured distance may be too small or too large for the camera 120 to adjust its zoom level to take a clear image/video of the eyes of the user. In such cases, the user device 110 may post a notice on the user interface or chat window requesting that the user change her/his position with respect to the camera 120 so that the eyes/face of the user is in the range that the camera 120 can focus.

In some embodiments, the settings may also include pre-set parameters to choose from for each of the various properties of the camera 120, such as but not limited to the exposure, iris size, backlight compensation, brightness, saturation, sharpness, gamma, contrast, etc. In some instances, the parameters may be within set limits and if the selected parameter of a property does not result in an image and/or video that is acceptable for diagnosis/treatment of the eye disease or condition of the user, a notice may be posted on the user interface 190 of the user device to inform the user of the inadequacy and request corrections be made.

In some embodiments, after the camera 120 captures the image/video of the eye of the user (e.g., the capturing having been activated by the user pressing a key on the keyboard), the image/video of the eye may be transmitted to the remote server 170 as part of PHI data of the patient over the network 160 via the bidirectional communication link coupling the user interface 190 (e.g., and as such the input interface) to the remote server 170. Further, in some instances, the bidirectional communication link may also include a link connecting the user device 110 with a storage server (e.g., cloud server) 140 that includes a database 150. In such cases, instead of or in addition to transmitting the PHI data including the captured image/video to the remote server 170, the user device 110 may also transmit the PHI including the captured image/video to the cloud server 140 for storage. In some instances, the bidirectional communication links connecting the user device 110 to the remote server 170 and/or the cloud server 140 may be encrypted and may utilize SSL to securely transport the PHI to the remote server 170 and/or the cloud server 140 in a manner that is HIPAA-compliant. Further, the storage server 140 may also be HIPAA-compliant, i.e., store the PHI data in a secure manner consistent with the requirements of HIPAA. For instance, the transport and storage of the PHI data may be anonymized, i.e., the PHI data may be processed to remove and/or obfuscate personally identifying information (PII) of the patient/user to which the PHI data belongs.

Figure 2:
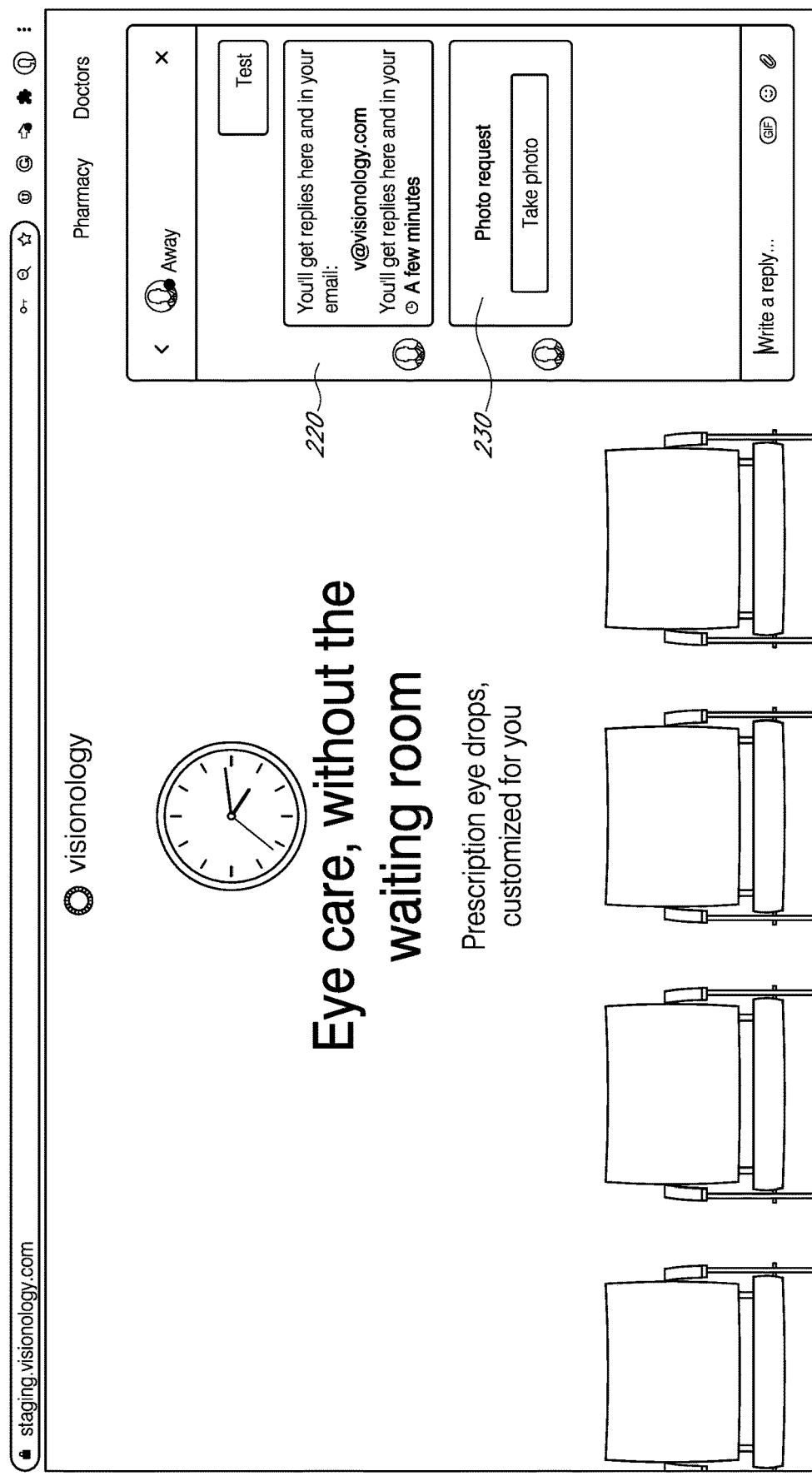
FIG. 2 shows an example illustration of a user interface having a chat window that is configured to facilitate the remote capturing of a media, according to various embodiments of the present disclosure.

FIG. 2 shows an example illustration 200 of a user interface having a chat window that is configured to facilitate the remote capturing of a media, according to various embodiments of the present disclosure. In some embodiments, a user may launch from her/his user device a user interface 210 having an input interface 220 (can also be referred to herein as chat window 220) that allows the user to remotely communicate with a remote server (e.g., such as remote server 170 of FIG. 1) that is configured to request authorization from the user to remotely capture a media (e.g., image, video, etc.) of the user. For example, the user interface 210 can be an application user interface of an application operating on the user device or a web browser. In some instances, after the launching of the user interface 210 on the user device by the user, the input interface or chat window 220 may automatically appear on the user interface 210.

In some instances, the user interface 210 and/or the chat window 220 may be linked to the remote server by a bidirectional communication link that is configured to secure the communication between the chat window 220 and the remote server. For example, the bidirectional communication link may be configured to encrypt the communications (e.g., texts, images, videos, etc.) that are exchanged between the user device (e.g., from the chat window 220) and the remote server. For instance, the communication link may utilize SSL protocols configured to secure data communications for facilitating the exchanges of the communications between the user device and the remote server. In some cases, the bidirectional communication link may be configured to anonymize the exchanged communications so that PHI in the communications may be obfuscated or removed. In some instances, the communication link may be HIPAA-compliant in that the communication link may comply with the requirements of HIPAA related to securing the transmission and storage of medical data (e.g., encrypting and/or anonymizing medical data when transmitting and storing, etc.).

In some embodiments, the remote server may transmit a prompt 230 or a request, via the chat window 220, for the user of the user device to provide the remote server with a media (e.g. image, video, etc., of the eye(s) of the user). In some instances, the prompt 230 may be in response to an indication from the user indicating a need for diagnosis or treatment of an eye disease or a condition. For example, the user may input a message into the chat window 220 indicting that the user may be having a medical issue or problem with the user's eyes (e.g., the message including symptoms). In some instances, the prompt 230 may be automatic, i.e., the prompt 230 may be displayed in the chat window automatically upon the launching of the chat window 220.

In some embodiments, the prompt 230 from the remote server may be a request for an authorization from the user of the user device so that the user device may launch its camera to capture an image or video of the user's eye(s). That is, the prompt 230 may be a request from the remote server to be allowed to remotely capture an image or video of the eye(s) of the user. In some embodiments, upon receiving an authorization from the user (e.g., via the user tapping or clicking on the prompt 230 authorizing the request), the user device may activate or launch its camera.

In some embodiments, the user device may determine a focus or zoom level for the camera to capture an image or video of an eye of the user facing the camera based on a type of the user device, examples of types of user devices including mobile device, handheld device, portable device, or combination thereof, or non-mobile device, non-handheld device, non-portable device, or combination thereof. In some embodiments, the user device, the remote server and/or the application operating on the user device and associated with the launched application user interface 210 may be configured to detect the type of the user device. For instance, the processor of the user device may access information stored in a memory of the user device identifying the type of the user device. As another example, the remote server may communicate with the user to detect a type of the user device and provide/transmit the information to the user device. And yet another example, the application may also detect the type of the user device and provide the same information to the user device. In some embodiments, upon obtaining the information identifying the type of the user device, the user device (e.g., or processor thereof) may determine the focus or zoom level of the camera for capturing a media (e.g., image, video, etc.) of an eye of the user facing the camera based on the type of the user device. For instance, the user device may choose a first pre-set zoom level for the camera to capture the media if the type of the user device is a handheld and/or portable user device type and a second pre-set zoom level if the type of the user device is a non-handheld and/or non-portable user device type. And because users can readily adjust the distance between the user device and their faces/eyes when the user device is handheld or portable, in some cases, the first pre-set zoom level may be lower than the second pre-set zoom level, i.e., the camera may zoom less when the user device is a handheld and/or portable user device compared to when the user device is a non-handheld and/or non-portable user device. In such cases, the user device may adjust the zoom level of the camera to at least substantially match the selected pre-set zoom level.

In some embodiments, the user device may be configured to use a facial recognition module operating therein to estimate or measure the distance between the camera on the user device and the eye of the user facing the camera. In some instances, the user device may adjust the zoom level of the camera based on the estimated or measured distance, i.e., the user device may select a zoom level of the camera so that the camera focuses on the eye of the user facing the camera. In some cases, the estimated or measured distance may be outside of a range within which the user device is configured to adjust the zoom level of the camera, i.e., the estimated or measured distance may be less than a minimum threshold or greater than a maximum threshold of the range of distances within which the user device may adjust the zoom level of the camera to capture a focused image or video of the eye of the user. In such cases, the user device may provide a message in the chat window 220 instructing the user to adjust (i.e., reduce or increase) the distance accordingly.

FIGS. 3A-3C show example illustrations of the remote capturing of a user's eyes via a chat window operating on a user interface that is bidirectionally linked to a remote server, according to various aspects of the present disclosure. In some embodiments, as discussed above, the user device may determine a focus or zoom level for capturing an image or video of the eye of a user facing the camera of the user device, and adjust the zoom of the camera accordingly based on the determined zoom level (e.g., to at least substantially match the determined zoom level). In some instances, the scene 310 to be captured by the image or video may appear in the chat window 320, in some cases with an outline or indication 330 superimposed thereon to guide the user when facing the camera. In some embodiments, the chat window 320 may include a button 340 thereon that allows the user to activate the camera of the user device (e.g., by tapping or clicking on the button 340) so that the camera captures the image or video displayed in the chat window 320. In some instances, the camera may be configured such that an activation of a key on a keyboard of the user device (e.g., space bar or "Enter" key being pressed) may trigger the camera to capture the image or video displayed in the chat window 320. In some embodiments, images or videos of both eyes of the user may be captured and transmitted to the remote server or a storage server (e.g., cloud server) from the chat window 320. In some embodiments, as discussed above, the communication between the chat window or user interface including the chat window and the remote server may be encrypted (e.g., and anonymized so that PII in the captured image/video may be obfuscated/removed to comply with the requirements of HIPAA). That is, the captured media (e.g., images, videos, etc.) may be encrypted when transmitted to the remote server and/or the secure cloud server. Further, the storage of the media in the storage server may also be encrypted and anonymized.

Figure 4:
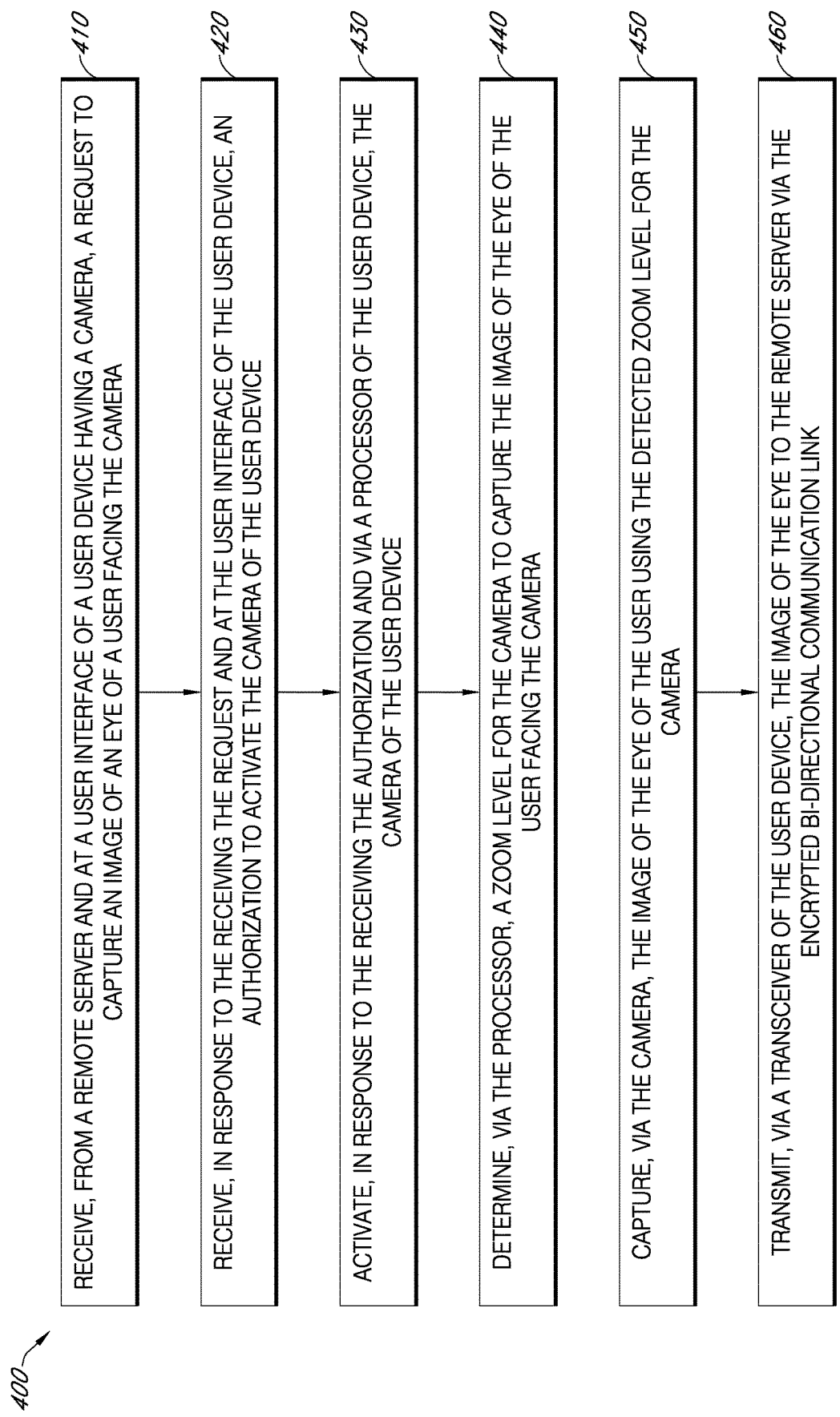
FIG. 4 is a flowchart illustrating a method of remotely capturing an image of eyes of a user via a user interface bidirectionally linked to a remote server, according to various aspects of the present disclosure.

FIG. 4 is a flowchart illustrating a method 400 of remotely capturing an image of eyes of a user via a user interface bidirectionally linked to a remote server, according to various aspects of the present disclosure. The various steps of the method 400, which are described in greater detail above, may be performed by one or more electronic processors, for example by the processors of the user device 110. Further, it is understood that additional method steps may be performed before, during, or after the steps 410-460 discussed below. In addition, in some embodiments, one or more of the steps 410-460 may also be omitted. Further, in some embodiments, steps 410-460 may be performed in different order than shown in FIG. 4.

The method 400 includes a step 410 to receive, from a remote server and at a user interface of a user device having a camera, a request to capture an image of an eye of a user facing the camera. In some embodiments, the user interface may be in communication with the remote server via an encrypted bi-directional communication link. Further, the remote server may be configured to anonymize data communicated thereto from the user device.

The method 400 includes a step 420 to receive, in response to the receiving the request and at the user interface of the user device, an authorization to activate the camera of the user device.

The method 400 includes a step 430 to activate, in response to the receiving the authorization and via a processor of the user device, the camera of the user device.

The method 400 includes a step 440 to determine, via the processor, a zoom level for the camera to capture the image of the eye of the user facing the camera.

The method 400 includes a step 450 to capture, via the camera, the image of the eye of the user using the determined zoom level for the camera.

The method 400 includes a step 460 to transmit, via a transceiver of the user device, the data including the captured image of the eye to the remote server via the encrypted bi-directional communication link. In some embodiments, the encrypted bi-directional communication link is HIPAA-compliant in that the communication link may comply with the requirements of HIPAA related to securing the transmission and storage of medical data.

In some embodiments, the method 400 further comprises detecting a type of the user device; and selecting a pre-set zoom level of the camera based on the type of the user device. In some instances, the type of the user device includes a portable user device or a non-portable user device; and the pre-set zoom level corresponding to the non-portable user device is greater than the pre-set zoom level corresponding to the portable user device.

In some embodiments, the method 400 further comprises detecting a distance between the eye of the user and the camera of the user device using a facial recognition module of the user device; and adjusting the zoom level based on the detected distance to focus the camera on the eye of the user. In some instances, the method 400 further comprises determining that the adjusted zoom level is not adequate to focus the camera on the eye of the user; and providing instruction, via the user interface of the user device, for the user to increase or decrease the distance between the eye of the user and the camera of the user device.

In some embodiments, the method 400 further comprises adjusting a property of the camera prior to the capturing the image of the eye of the user. In some instances, the property of the camera includes an exposure level of the camera, a saturation level of the camera, a sharpness level of the camera, a backlight compensation level of the camera, a contrast level of the camera, or a brightness level of the camera.

Figure 5:
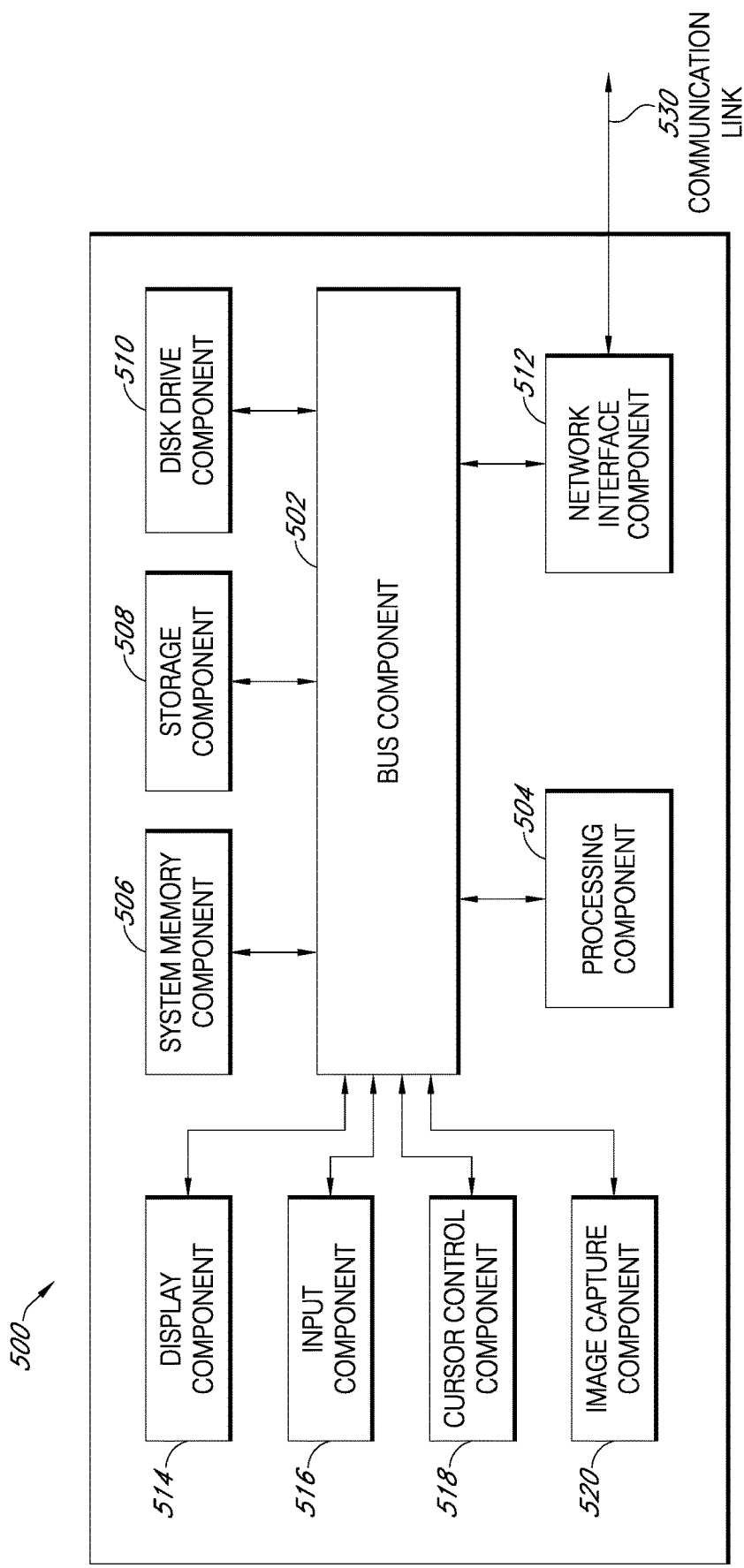
FIG. 5 is an example computer system, according to various aspects of the present disclosure.

FIG. 5 is a block diagram of a computer system 500 suitable for implementing various methods and devices described herein, for example, the user device 110, the secure cloud server 140, and the remote server 106. In various implementations, the devices capable of performing the steps may comprise a network communications device (e.g., mobile cellular phone, laptop, personal computer, tablet, etc.), a network computing device (e.g., a network server, a computer processor, an electronic communications interface, etc.), or another suitable device. Accordingly, it should be appreciated that the devices capable of implementing the aforementioned servers and modules, and the various method steps of the method 400 discussed above may be implemented as the computer system 500 in a manner as follows.

In accordance with various embodiments of the present disclosure, the computer system 500, such as a network server or a mobile communications device, includes a bus component 502 or other communication mechanisms for communicating information, which interconnects subsystems and components, such as a computer processing component 504 (e.g., processor, micro-controller, digital signal processor (DSP), etc.), system memory component 506 (e.g., RAM), static storage component 508 (e.g., ROM), disk drive component 510 (e.g., magnetic or optical), network interface component 512 (e.g., modem or Ethernet card), display component 514 (e.g., cathode ray tube (CRT) or liquid crystal display (LCD)), input component 516 (e.g., keyboard), cursor control component 518 (e.g., mouse or trackball), and image capture component 520 (e.g., analog or digital camera such as camera 120). In one implementation, disk drive component 510 may comprise a database having one or more disk drive components.

In accordance with embodiments of the present disclosure, computer system 500 performs specific operations by the processor 504 executing one or more sequences of one or more instructions contained in system memory component 506. Such instructions may be read into system memory component 506 from another computer readable medium, such as static storage component 508 or disk drive component 510. In other embodiments, hard-wired circuitry may be used in place of (or in combination with) software instructions to implement the present disclosure. In some embodiments, the various components of the camera 120, the facial recognition module 130, the remote media capture module 180, and the user interface 190 may be in the form of software instructions that can be executed by the processor 504 to automatically perform context-appropriate tasks on behalf of a user.

Logic may be encoded in a computer readable medium, which may refer to any medium that participates in providing instructions to the processor 504 for execution. Such a medium may take many forms, including but not limited to, non-volatile media and volatile media. In some embodiments, the computer readable medium is non-transitory. In various implementations, non-volatile media includes optical or magnetic disks, such as disk drive component 510, and volatile media includes dynamic memory, such as system memory component 506. In one aspect, data and information related to execution instructions may be transmitted to computer system 500 via a transmission media, such as in the form of acoustic or light waves, including those generated during radio wave and infrared data communications. In various implementations, transmission media may include coaxial cables, copper wire, and fiber optics, including wires that comprise bus 502.

Some common forms of computer readable media include, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, carrier wave, or any other medium from which a computer is adapted to read. These computer readable media may also be used to store the various components of the user device 110 (e.g., the facial recognition module 130, etc.), the secure cloud server 140, or the remote server 170 (e.g., the remote media capture module 180).

In various embodiments of the present disclosure, execution of instruction sequences to practice the present disclosure may be performed by computer system 500. In various other embodiments of the present disclosure, a plurality of computer systems 500 coupled by communication link 530 (e.g., a communications network, such as a LAN, WLAN, PTSN, and/or various other wired or wireless networks, including telecommunications, mobile, and cellular phone networks) may perform instruction sequences to practice the present disclosure in coordination with one another.

Computer system 500 may transmit and receive messages, data, information and instructions, including one or more programs (i.e., application code) through communication link 530 and communication interface 512. Received program code may be executed by computer processor 504 as received and/or stored in disk drive component 510 or some other non-volatile storage component for execution. The communication link 530 and/or the communication interface 512 may be used to conduct electronic communications among the user device 110, the secure cloud server 140, and the remote server 170.

Recitations of Some Embodiments of the Present Disclosure

Embodiment 1: A method, comprising: receiving, from a remote server and at a user interface of a user device having a camera, a request to capture an image of an eye of a user facing the camera, the user interface in communication with the remote server via an encrypted bi-directional communication link and the remote server configured to anonymize data communicated thereto from the user device; receiving, in response to the receiving the request and at the user interface of the user device, an authorization to activate the camera of the user device; activating, in response to the receiving the authorization and via a processor of the user device, the camera of the user device; determining, via the processor, a zoom level for the camera to capture the image of the eye of the user facing the camera; capturing, via the camera, the image of the eye of the user using the determined zoom level for the camera; and transmitting, via a transceiver of the user device, the data including the captured image of the eye to the remote server via the encrypted bi-directional communication link.

Embodiment 2: The method of embodiment 1, further comprising: detecting a type of the user device; and selecting a pre-set zoom level of the camera based on the type of the user device.

Embodiment 3: The method of embodiment 2, wherein: the type of the user device includes a portable user device or a non-portable user device; and the pre-set zoom level corresponding to the non-portable user device is greater than the pre-set zoom level corresponding to the portable user device.

Embodiment 4: The method of any of embodiments 1-3, further comprising: detecting a distance between the eye of the user and the camera of the user device using a facial recognition module of the user device; and adjusting the zoom level based on the detected distance to focus the camera on the eye of the user.

Embodiment 5: The method of embodiment 4, further comprising: determining that the adjusted zoom level is not adequate to focus the camera on the eye of the user; and providing instruction, via the user interface of the user device, for the user to increase or decrease the distance between the eye of the user and the camera of the user device.

Embodiment 6: The method of any of embodiments 1-5, further comprising: adjusting a property of the camera prior to the capturing the image of the eye of the user.

Embodiment 7: The method of embodiment 6, wherein the property of the camera includes an exposure level of the camera, a saturation level of the camera, a sharpness level of the camera, a backlight compensation level of the camera, a contrast level of the camera, or a brightness level of the camera.

Embodiment 8: A system, comprising: a memory; a processor coupled to the memory and configured to, when executing instructions stored on the memory, to cause the system to perform the methods of embodiments 1-7.

Embodiment 9: A non-transitory computer-readable medium (CRM) having program code recorded thereon, the program code comprises code for causing a system to perform the methods of embodiments 1-7.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software, in accordance with the present disclosure, such as computer program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein. It is understood that at least a portion of the user device 110 (e.g., the facial recognition module 130, etc.), the secure cloud server 140, and the remote server 170 (e.g., the remote media capture module 180) may be implemented as such software code.

It should be appreciated that like reference numerals are used to identify like elements illustrated in one or more of the figures, wherein these labeled figures are for purposes of illustrating embodiments of the present disclosure and not for purposes of limiting the same.

All publications mentioned herein are incorporated herein by reference in their entirety for the purpose of describing and disclosing devices, compositions, formulations and methodologies which are described in the publication and which might be used in connection with the present disclosure.

As used herein, the terms "comprise", "comprises", "comprising", "contain", "contains", "containing", "have", "having", "include", "includes", and "including" and their variants are not intended to be limiting, are inclusive or open-ended and do not exclude additional, unrecited additives, components, integers, elements or method steps. For example, a process, method, system, composition, kit, or apparatus that comprises a list of features is not necessarily limited only to those features but may include other features not expressly listed or inherent to such process, method, system, composition, kit, or apparatus.

The foregoing disclosure is not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, persons of ordinary skill in the art will recognize that changes may be made in form and detail without departing from the scope of the present disclosure. Thus, the present disclosure is limited only by the claims.

What is claimed is:

1. A method, comprising:
receiving, from a remote server and at a user interface of a user device having a camera, a request to capture an image of an eye of a user facing the camera, the user interface in communication with the remote server via an encrypted bi-directional communication link and the remote server configured to anonymize data communicated thereto from the user device;
receiving, in response to the receiving the request and at the user interface of the user device, an authorization to activate the camera of the user device;
activating, in response to the receiving the authorization and via a processor of the user device, the camera of the user device;
detecting a distance between the eye of the user and the camera of the user device using a facial recognition module of the user device;
adjusting a zoom level based on the detected distance to focus the camera on the eye of the user;
determining that the adjusted zoom level is not adequate to focus the camera on the eye of the user;
providing instruction, via the user interface of the user device, for the user to increase or decrease the distance between the eye of the user and the camera of the user device;
determining, via the processor, the zoom level for the camera to capture the image of the eye of the user facing the camera;
capturing, via the camera, the image of the eye of the user using the determined zoom level for the camera; and
transmitting, via a transceiver of the user device, the data including the captured image of the eye to the remote server via the encrypted bi-directional communication link.

2. The method of claim 1, further comprising:
detecting a type of the user device; and
selecting a pre-set zoom level of the camera based on the type of the user device.

3. The method of claim 2, wherein:
the type of the user device includes a portable user device or a non-portable user device;
and the pre-set zoom level corresponding to the non-portable user device is greater than the pre-set zoom level corresponding to the portable user device.

4. The method of claim 1, further comprising: adjusting a property of the camera prior to the capturing the image of the eye of the user.

5. The method of claim 4, wherein the property of the camera includes an exposure level of the camera, a saturation level of the camera, a sharpness level of the camera, a backlight compensation level of the camera, a contrast level of the camera, or a brightness level of the camera.

6. A system, comprising:
a non-transitory memory storing instructions; and
one or more hardware processors coupled to the non-transitory memory and configured to read the instructions from the non-transitory memory to cause the system to perform operations compromising
receiving, from a remote server and at a user interface of a user device having a camera, a request to capture an image of an eye of a user facing the camera, the user interface in communication with the remote server via an encrypted bi-directional communication link and the remote server configured to anonymize data communicated thereto from the user device;
receiving, in response to the receiving the request and at the user interface of the user device, an authorization to activate the camera of the user device;
activating, in response to the receiving the authorization and via a processor of the user device, the camera of the user device;
detecting a distance between the eye of the user and the camera of the user device using a facial recognition module of the user device;
adjusting a zoom level based on the detected distance to focus the camera on the eye of the user;
determining that the adjusted zoom level is not adequate to focus the camera on the eye of the user;
providing instruction, via the user interface of the user device, for the user to increase or decrease the distance between the eye of the user and the camera of the user device;
determining, via the processor, the zoom level for the camera to capture the image of the eye of the user facing the camera;

capturing, via the camera, the image of the eye of the user using the determined zoom level for the camera; and transmitting, via a transceiver of the user device, the data including the captured image of the eye to the remote server via the encrypted bi-directional communication link.

7. The system of claim 6, wherein the operations further comprise:

detecting a type of the user device; and selecting a pre-set zoom level of the camera based on the type of the user device.

8. The system of claim 7, wherein:

the type of the user device includes a portable user device or a non-portable user device; and the pre-set zoom level corresponding to the non-portable user device is greater than the pre-set zoom level corresponding to the portable user device.

9. The system of claim 6, wherein the operations further comprise: adjusting a property of the camera prior to the capturing the image of the eye of the user.

10. The system of claim 9, wherein the property of the camera includes an exposure level of the camera, a saturation level of the camera, a sharpness level of the camera, a backlight compensation level of the camera, a contrast level of the camera, or a brightness level of the camera.

11. A non-transitory computer-readable medium (CRM) having stored thereon computer-readable instructions executable to cause performance of operations comprising:

receiving, from a remote server and at a user interface of a user device having a camera, a request to capture an image of an eye of a user facing the camera, the user interface in communication with the remote server via an encrypted bi-directional communication link and the remote server configured to anonymize data communicated thereto from the user device;

receiving, in response to the receiving the request and at the user interface of the user device, an authorization to activate the camera of the user device;

activating, in response to the receiving the authorization and via a processor of the user device, the camera of the user device;

detecting a distance between the eye of the user and the camera of the user device using a facial recognition module of the user device;

adjusting the zoom level based on the detected distance to focus the camera on the eye of the user;

determining that the adjusted zoom level is not adequate to focus the camera on the eye of the user;

providing instruction, via the user interface of the user device, for the user to increase or decrease the distance between the eye of the user and the camera of the user device;

determining, via the processor, the zoom level for the camera to capture the image of the eye of the user facing the camera;

capturing, via the camera, the image of the eye of the user using the determined zoom level for the camera; and transmitting, via a transceiver of the user device, the data including the captured image of the eye to the remote server via the encrypted bi-directional communication link.

12. The non-transitory CRM of claim 11, wherein the operations further comprise:

detecting a type of the user device; and selecting a pre-set zoom level of the camera based on the type of the user device.

13. The non-transitory CRM of claim 12, wherein:

the type of the user device includes a portable user device or a non-portable user device; and the pre-set zoom level corresponding to the non-portable user device is greater than the pre-set zoom level corresponding to the portable user device.

14. The non-transitory CRM of claim 11, wherein the operations further comprise: adjusting a property of the camera prior to the capturing the image of the eye of the user.

15. The non-transitory CRM of claim 9, wherein the property of the camera includes an exposure level of the camera, a saturation level of the camera, a sharpness level of the camera, a backlight compensation level of the camera, a contrast level of the camera, or a brightness level of the camera.

* * * * *